(12) United States Patent
Hishinuma

(10) Patent No.: US 6,952,959 B2
(45) Date of Patent: Oct. 11, 2005

(54) METHOD OF DESIGNING A HEAT SEAL WIDTH

(76) Inventor: Kazuo Hishinuma, 1232, Ogura, Saiwai-ku, Kawasaki-shi, Kanagawa 212-0054 (JP)

( * ) Notice: Subject to any disclaimer, the term of this patent is extended or adjusted under 35 U.S.C. 154(b) by 83 days.

(21) Appl. No.: 10/772,549

(22) Filed: Feb. 5, 2004

(65) Prior Publication Data

US 2004/0255664 A1 Dec. 23, 2004

(30) Foreign Application Priority Data

Jun. 20, 2003 (JP) .............................. 2003-201368
Jun. 20, 2003 (JP) .............................. 2003-201370

(51) Int. Cl.$^7$ .............................................. G01L 5/04
(52) U.S. Cl. ........................... 73/159; 73/828; 73/834; 73/838; 73/807; 73/588
(58) Field of Search ................... 73/159–160, 828–830, 73/834, 838–851, 807–810, 821, 582–588

(56) References Cited

U.S. PATENT DOCUMENTS

| | | | |
|---|---|---|---|
| 4,550,613 A * | 11/1985 | Lehtikoski et al. ............. | 73/159 |
| 4,979,394 A * | 12/1990 | Higo et al. .................... | 73/602 |
| 5,527,622 A * | 6/1996 | Kato et al. .................... | 428/481 |
| 6,568,533 B1 * | 5/2003 | Tanaka et al. ................. | 206/484 |
| 6,689,177 B2 * | 2/2004 | Sugiyama et al. ............ | 29/623.2 |
| 2002/0151438 A1 * | 10/2002 | Mihara et al. ................. | 428/195 |

* cited by examiner

Primary Examiner—Edward Lefkowitz
Assistant Examiner—Alandra Ellington
(74) Attorney, Agent, or Firm—Flynn, Thiel, Boutell & Tanis, P.C.

(57) ABSTRACT

This invention provides a method of designing a suitable heat seal width which is more resistant to unsealing than conventional heat-sealing, which involves the steps of; (1) heat-sealing a test piece of a sheet to be heat-sealed at a temperature lower than the fusion temperature of a heat seal portion of the sheet, (2) heat-sealing another test piece of the sheet at a temperature at or higher than the fusion temperature, (3) pulling to peel a heat-sealed portion of each test piece, and measuring the pull strength variation with peel length, (4) calculating the peel energy in various peel length as of the test piece heat-sealed at a temperature lower than the fusion temperature of the heat seal portion of the sheet by integrating the pull strength variation, (5) calculating the peel energy of the test piece heat-sealed at the temperature at or higher than the fusion temperature by integrating the pull strength variation up to rupture at a heat-sealed portion, and (6) setting the heat seal width at a peel length having a peel energy higher than the peel energy of the test piece heat-sealed at the temperature at or higher than the fusion temperature.

9 Claims, 5 Drawing Sheets

METHOD OF DESIGNING A HEAT SEAL WIDTH

BACKGROUND OF THE INVENTION

The invention relates to a method of designing a heat seal width of a bag or the like.

Heat-sealing is now widely utilized for making bags, sealing the opening of containers and so on. The heat-sealing is required not to separate or rupture at a heat-sealed portion by shock or load during physical distribution or serving. Therefore, heat-sealing is, in general, conducted so as to fuse the heat-sealed portion enough, and when the strength at heat-sealed portion is not enough, such as rupture occurred, skilled artizan has solved this problem by increasing the thickness of the sheet to be heat-sealed. However, to thicken the sheet increases its manufacturing cost.

On the other hand, the heat seal width is decided empirically, for example, in balance with the size of bag.

SUMMARY OF THE INVENTION

An object of the invention is to provide a heat seal which has an improved strength and reduced manufacturing cost, thereby.

The inventor investigated eagerly in order to achieve the above object, and found that there is a region resistant to unsealing more than conventional heat-sealing.

That is, when pulling a conventional heat-sealed portion of two sheets in opposite directions, i.e. so as to separate them from each other, the heat-sealed portion peels and then ruptures (including delamination). On the other hand, when heat-sealing is carried out near or slightly lower than the fusion temperature, the heat-sealed portion gradually peels with pulling, the energy for peeling gradually increases with peel length, and exceeds the peel energy consumed until rupture. That is, a heat-sealing resistant to unsealing more than conventional heat-sealing can be obtained by adjusting the heat-sealing temperature and heat seal width.

Heretofore, there was no means for discriminating the latter heat seal (peel seal) from the former heat seal (rupture seal). The inventor devised this means, and completed the invention with a high reproducibility of heat-sealing utilizing this means.

The present invention has been achieved based on the above findings, and provides, a method of designing a heat seal width which comprises;
(1) heat-sealing a test piece of a sheet to be heat-sealed at a temperature lower than the fusion temperature of a heat seal portion of the sheet,
(2) heat-sealing another test piece of the sheet at a temperature at or higher than the fusion temperature,
(3) pulling to peel a heat-sealed portion of each test piece, and measuring the pull strength variation with peel length,
(4) calculating the peel energy in various peel lengths of the test piece heat-sealed at a temperature lower than the fusion temperature of the heat seal portion of the sheet by integrating the pull strength variation,
(5) calculating the peel energy of the test piece heat-sealed at the temperature at or higher than the fusion temperature by integrating the pull strength variation up to rupture at the heat-sealed portion, and
(6) setting the heat seal width at a peel length having a peel energy higher than the peel energy of the test piece heat-sealed at the temperature at or higher than the fusion temperature, and a method of designing heat seal width which comprises;
(1) repeating heat-sealing of test pieces of a sheet to be heat-sealed at varying heat-sealing temperatures around the fusion temperature of a heat seal portion of the sheet,
(2) pulling to peel a heat-sealed portion of each test piece, and measuring the pull strength variation with peel length,
(3) calculating the peel energy in various peel lengths of each test piece at each heat-sealing temperature lower that the fusion temperature by integrating the pull strength variation to determine a variation of the peel energy with the heat-sealing temperature at various peel lengths,
(4) calculating the peel energy of at least one test piece heat-sealed at a temperature at or higher than the fusion temperature by integrating the pull strength variation up to rupture at a heat-sealed portion, and
(5) setting the heat seal width at a peel length having a peel energy higher than the peel energy of the test piece heat-sealed at a temperature at or higher than the fusion temperature.

Figure 1:
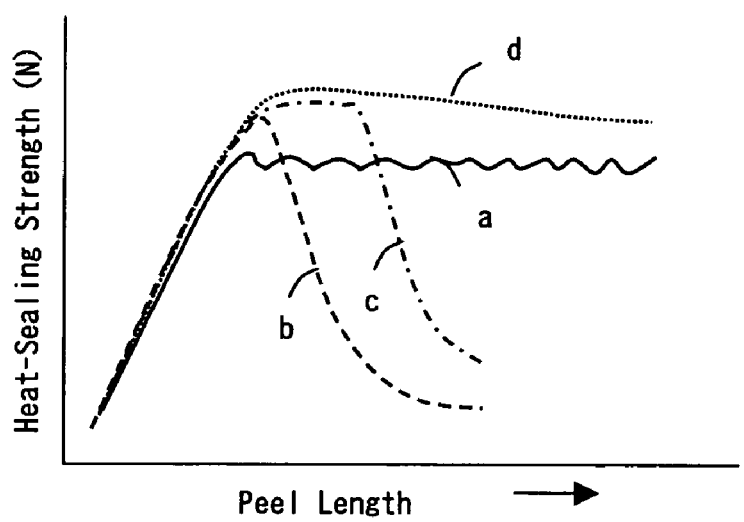
FIG. 1 is a graph showing variation patterns of heat-sealing strength with peel length indicating peel seal, rupture seal and the like measured by the JIS method.

1 . . . Heating block
2 . . . Minute temperature sensor
3 . . . Teflon sheet
4 . . . Minute temperature sensor
5 . . . Test piece
6 . . . Digital recorder
10 . . . Moving jaw
11 . . . Fixed jaw
12 . . . Force gauge
13 . . . Digital recorder
14 . . . Personal computer

DETAILED DESCRIPTION OF THE INVENTION

The test piece subjected to the method of the invention is a real sheet to be heat-sealed which may be a single layer sheet or multilayer sheet. The thickness of the sheet ranges about from 10 µm to 2 mm, usually about from 20 µm to 200 µm. The sheet has a heat seal portion, usually a heat seal layer. The heat seal layer is made of any thermoplastic material, preferably a polyolefin resin such as a polyethylene resin, L-LDPE resin, ethylene-propylene copolymer resin, and polypropylene. The thickness of the heat seal layer is not limited, but in general, is about from 10 µm to 1000 µm.

The test piece is usually a pair of strips preferably having a width of 10 to 25.4 mm, particularly 10 to 15 mm, and a length of 60 to 100 mm, particularly 30 to 80 mm.

The apparatus for heat-sealing may be any heat-sealing tester capable of controlling the heat-sealing temperature. However, a preferred apparatus is able to measure the exact temperature of the welding face, and for that purpose, the heat-sealing tester developed by the inventor (U.S. Pat. No. 6,197,136 B1) is preferred.

The inventor found that heat-sealed state depends on mainly the heating temperature and time, and the nipping pressure does not greatly influence the heat-sealed state. That is, the nipping pressure of both faces is not so important, and in common, it is enough to nip the test piece to be heat-sealed so as to contact both welding faces. A conventional nip pressure is in the range of about 0.05 to 0.2 MPa, and it is preferable to adjust the nip pressure to that of the real heat sealer.

The heating time is made constant in order to make uniform the time for preparation of the samples. A suitable heating time can be set as follows: That is, a pair of test strips nipped at a pressure of 0.1–0.2 MPa is heated to a prescribed temperature (which may be any temperature within the range to be tested) with the interposition of a minute temperature sensor, preferably 10 to 40 µm in thickness, until the temperature measured by the sensor becomes constant within the temperature variation of 0.1–0.2° C. This measurement may be made once, and the period is used as the heating time.

The heat-sealing (temperature on welding face) is varied around the fusion temperature (melting point), e.g. in the range from initiation of thermal adhesion to occurrence of thermal deterioration, or from −20° C. to +10° C., at an interval of 1–2° C. in the vicinity of the fusion temperature and then 5–10° C. apart therefrom.

When the heat-sealing test is carried out at two temperatures, one is lower than the fusion temperature of the heat seal portion, and the other is at or higher than the fusion temperature, the temperature lower than the fusion temperature is preferably lower than the fusion temperature by 1 to 20° C. On the other hand, the temperature at or higher than the fusion temperature is at or higher than the fusion temperature by 10° C.

Then, each heat-sealed test piece is attached to a tensile tester, and pulled to peel the heat-sealed portion at a constant speed to measure the variation of pull strength with time, i.e. with peel length. In order to remove error caused by the elongation of the test piece, it is preferable to shorten the test piece, such that the distance between the two jaws for fixing the free ends of the test piece becomes 20–30 mm.

As mentioned previously, there are two types of heat seal, i.e. peel seal and rupture seal. Heretofore, the suitability of the heat seal was evaluated by the measurement of heat-sealing strength and observation of peeled surface according to JIS Z 0238. However, there is no method of discriminating peel seal from rupture seal, and it is not established to conduct heat-sealing to form a peel seal in reproducible conditions.

In the invention, the peel seal is distinguished from the rupture seal as follows;

(1) repeating the heat-sealing of test pieces of a sheet to be heat-sealed obliquely with varying heat-sealing temperatures around the fusion temperature of a heat seal portion of the sheet, (2) pulling to peel a heat-sealed portion of each test piece, and measuring the pull strength variation with peel length to determine a maximum pull strength, (3) plotting the maximum pull strength against heat-sealing temperature, and (4) determining the position of the pull strength lower than the peak of the maximum pull strength by 20%, which is set from experimental results, by considering experimental error on the side of a higher heat-sealing temperature than the peak.

The above position is the boundary between the peal seal and the rupture seal.

The sum of the multiplication of pull strength by peel length is peel energy. Internal pressure is generated by adding external force to a sealed bag. When the stress per unit length (corresponding to the width in FIG. 8) generated by the internal pressure is greater than the pull strength of the welding face, peeling occurs. The energy generated by the internal pressure is consumed by the conversion into peel energy to reduce the stress generated in the bag. When the heat seal width is greater than the peel length, the advance of the peeling is stopped at the position where the stress generated in the bag is balanced with the pull strength per unit length.

In the specification, the heat-sealing strength is measured according to JIS Z 0238, and the pull strength is measured by the method of the invention.

A typical relationship between the heat-sealing strength and peel length measured according to JIS Z 0238 is shown in FIG. 1. In the figure, a indicates a pattern of peel seal, b indicates rupture seal, and c and d indicate abnormal heat seals. In the case of a, after reaching a pull strength of a certain value, the pull strength becomes almost constant, irrespective of pull length. In the case of b, the welding face is completely welded to generate rupture. That is, the stress generated by internal pressure is greater than the heat-sealing strength, and the heat seal line reaches the yield point without peeling to rupture at once. This phenomenon occurs by great impact induced by dropping or the like. In the case of c, fusion of the heat seal layer is uneven. It is rare to load stress to the heat seal line uniformly, and in some cases, the stress generated on the inside is concentrated to a width of 5 mm or less. In the case of d, the heat seal layer is once liquefied completely by high temperature or high nipping pressure to effuse out of a heat seal line. Since the heat seal line is thickened by the effused heat seal resin, the heat seal strength measured by a tensile tester is made great. However, this phenomenon is unfavorable because the effusion is not uniform.

Figure 2:
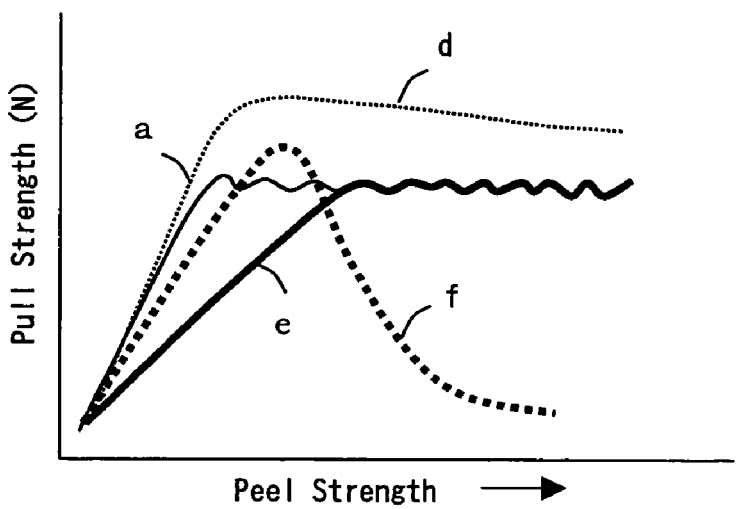
FIG. 2 is a graph showing variation patterns of pull strength with peel length indicating peel seal, rupture seal and the like measured by the method developed by the invention.

A typical relationship between the pull strength and peel length measured by the method of the invention (described in Example 1) is shown in FIG. 2. In the figure, a and d are the same as those in FIG. 1. e is a pull strength pattern in a peel seal region. Since peeling occurs in a form of a triangle from a point, the pull strength elevates in almost a straight line, and after reaching a 15 mm width line, the pull strength becomes constant as the same as the JIS value. On the other hand, f is a small strength pattern in rupture strength. In this case, since the heat seal resin effuses out to form polymer beads, rupture occurs easily by the concentration of stress to the beads portion. In the case of triangular peeling, rupture occurs with probability, and pull strength descends therefrom. Accordingly, the peak of the pull strength is lower than that of the heat-sealing strength measured by JIS.

Figure 11:
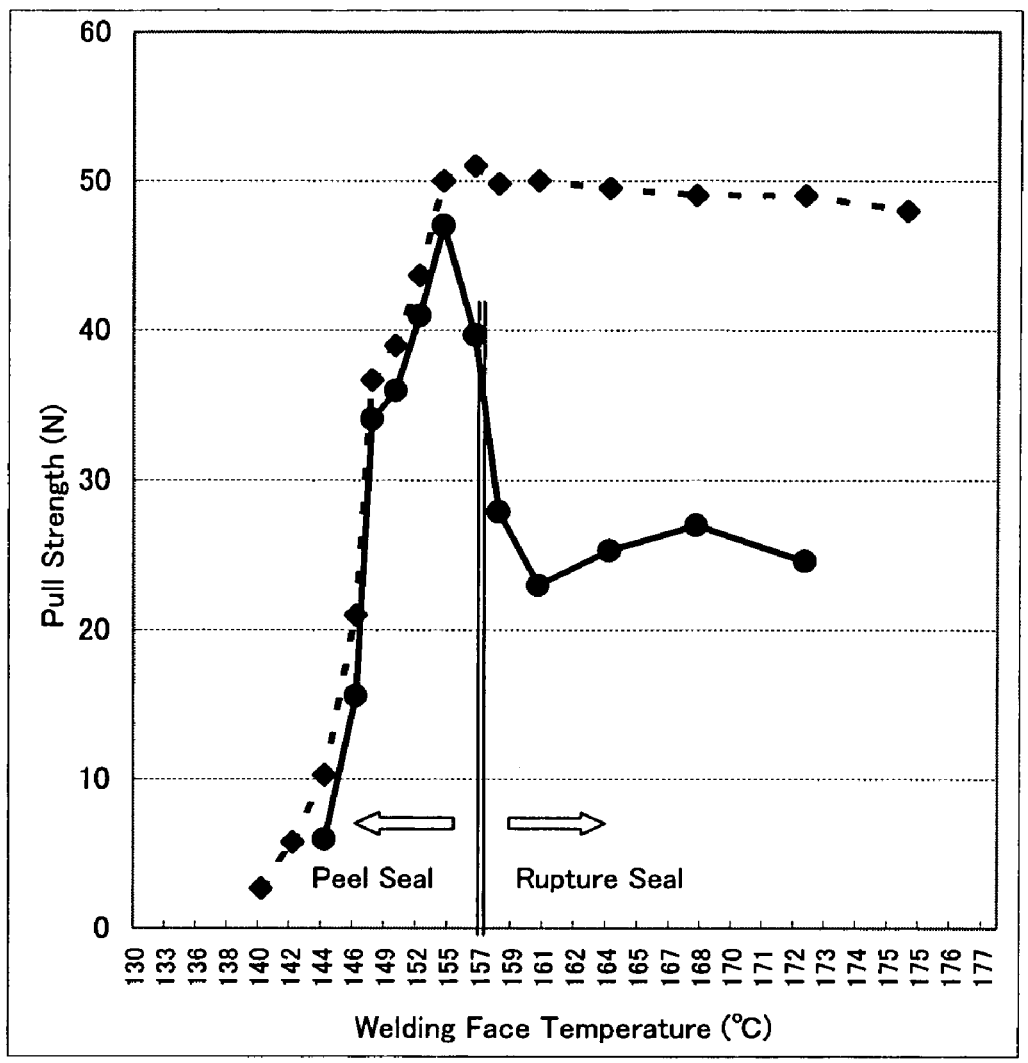
FIG. 11 is a graph showing the pull strength variation with heat-sealing temperature for the discrimination of a peel seal with a rupture seal.

By the lowering of the peak of the pull strength caused by oblique heat-sealing, differentiation of peel seal from rupture seal can be facilitated as shown in FIG. 11. A suitable heat seal angle is about 10 to 70 degrees, preferably 20 to 60 degrees, more preferably 30 to 45 degrees against the cross direction of test strip.

When heat seal width is designed by the data of two temperatures, it is preferable that one is at the peak (153° C. in FIG. 11), and the other is at a bottom (161° C. in FIG. 11).

In a high temperature region where rupture seal occurs surely, the peak of the pull strength lowers, and the rupture seal can be found easily.

Subsequently, the peel energy in various peel lengths of the test piece heat-sealed at a temperature lower than the fusion temperature of the heat seal portion of the sheet is calculated.

Figure 3:
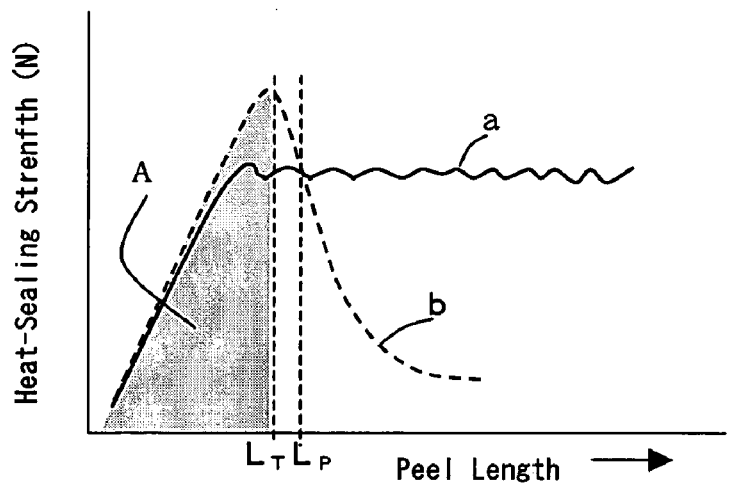
FIG. 3 is a graph showing schematic variation patterns of heat-sealing strength with peel length indicating peel seal and rupture seal for the explanation of peel energy.

Representative variation patterns of heat-sealing strength with peel length are shown in FIG. 3, wherein a indicates a pattern of peel seal and b indicates a pattern of rupture seal. Lt indicates a ruptured position and Lp indicates the cross point of line a and line b where both peel energies agree. The triangle portion indicated by A is the peel energy in rupture seal.

As mentioned above, the peel energy is the sum of the multiplication of pull strength by peel length, i.e., it is obtained by integrating the pull strength variation for each peel length. The temperature can be the same as the real heat-sealing temperature or selected from slightly lower than the fusion temperature.

Otherwise, it is also possible to calculate in various peel lengths of each test piece with various heat-sealing temperatures by integrating the pull strength variation to determine a variation of the peel energy with the heat-sealing temperature at various peel lengths to prepare a table or graph. The table or graph can be utilized for designing a heat-sealing temperature and heat seal width.

Then, a peel energy of at least one test piece heat-sealed at a temperature of or higher than the fusion temperature is also calculated by integrating the pull strength variation up to rupture at the heat-sealed portion. It is preferable to calculate the peel energy of the test pieces at various heat-sealing temperatures to determine a peak of peel energy variation in the rupture seal region.

By comparing the peel energy variation with peel length at a temperature lower than the fusion temperature with the peel energy of the test piece heat-sealed at a temperature at or higher than the fusion temperature, preferably at the peak of peel energy variation in a rupture seal region, a suitable heat seal width can be designed. That is, the heat seal width is set so that the peel energy for the heat seal width exceeds that in the rupture seal region. It is also preferable so as to have an air allowance, such that the peel energy for the heat seal width is greater than that in the rupture seal region by 10% or more, preferably 20% or more.

The method of the invention is applicable to various heat seal bags, such as one to four-sided fin seal bags, heat sealing of openings, and any other articles having a heat seal.

EXAMPLES

Example 1

Discrimination of Peel Seal from Rupture Seal

A commercial sheet for a retort pouch was subjected to testing which had a layer construction of 12 μm polyethylene terephthalate/7 μm aluminum/70 μm cast polypropylene. The polypropylene layer was the heat seal layer having a fusion temperature of about 153° C.

This sheet was cut into strips of 20 mm in width and 60 mm in length. Each of two strips were superimposed facing their heat seal layer to each other to prepare test pieces.

Figure 4:
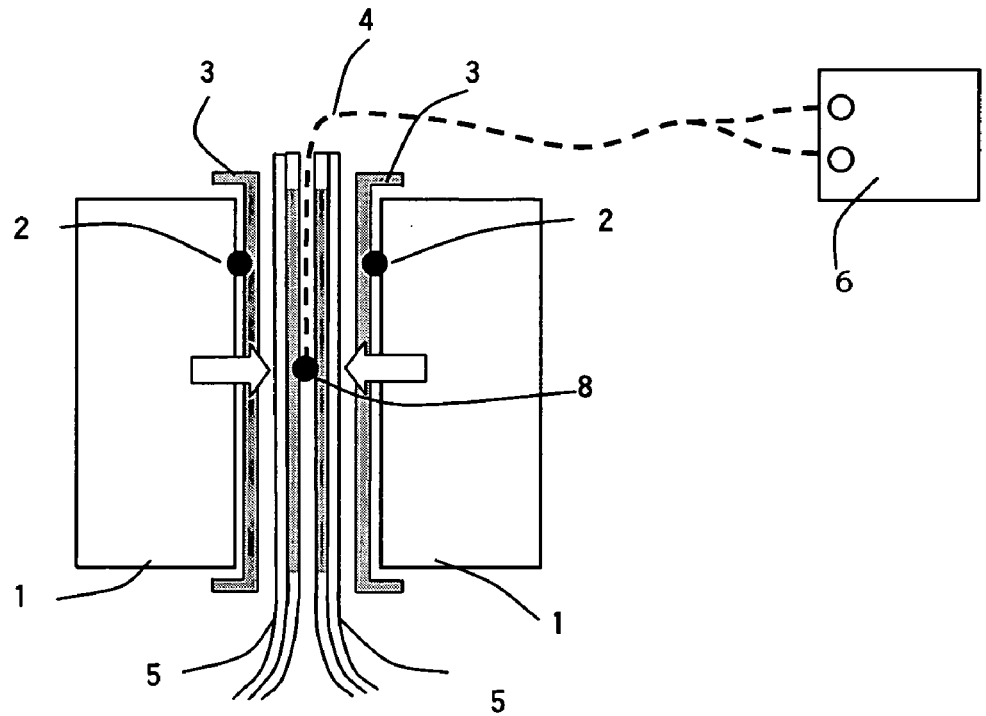
FIG. 4 illustrates the structure of a heat-sealing tester employed in the Examples schematically.

As the heat-sealing tester, an apparatus shown in FIG. 4 was used which was developed by the inventor (U.S. Pat. No. 6,197,136 B1). This apparatus was composed of two movable heating blocks 1,1 each having a heating face of 2 cm in width×8 cm in length. The surface temperature of each heating face can be measured by a minute temperature sensor 2 (RKC INSTRUMENT INC., diameter: 43 μm Φ) attached to each heating face. In order to unify the heating by decreasing the heating rate, each heating face was covered with a fluorocarbon resin (tradename: Teflon) sheet 3 having a thickness of 0.1–0.15 mm. Custom-made minute temperature sensors 4 (RKC INSTRUMENT INC., diameter: 10–40 μm) were inserted between the test strips of each test piece 5 wherein a dispersion of 0.1 to 0.2° C. occurred by the sensitivity of the sensor and measuring device. Each thermocouple 4 was connected to a digital recorder 6.

A suitable heating time was previously measured by heat-sealing a pair of the test strips 5 nipped at a pressure of 0.1–0.2 MPa at 180° C. with interposition of the minute temperature sensors 4 10–40 μm in thickness, until the temperature measured by the sensor 4 became constant within the temperature variation of 0.1–0.2° C., and set 20 seconds. By the operation, the temperature of the welding face agrees with the surface temperature of the heating block 1.

Heat-sealing was carried out obliquely at an angle of 30 to 45 degree against the cross direction of the test piece at various temperatures for 15 seconds with a nipping pressure of 0.1–0.2 MPa. The temperature was varied from 138° C. to 180° C. at intervals of about 2–5° C.

After heat-sealing, each test piece was cooled immediately by forcing (lower than 0.05 MPa) a metal block having an ordinary temperature thereon.

Figure 5:
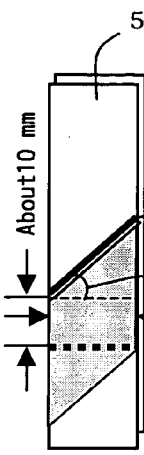
FIG. 5 is a plan view of a test piece used in Example 1.

Both side portions of the cooled test piece were slit leaving the central portion 15 mm in width with an accuracy of ±0.1 mm. By the cutting, the length of the entirely heat-sealed portion was made about 10 mm as shown in FIG. 5.

Figure 6:
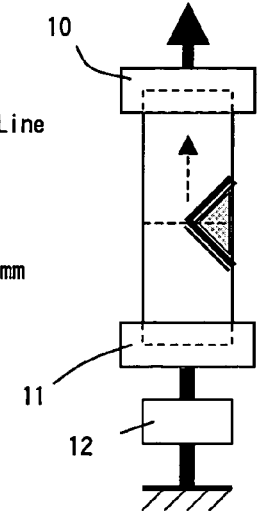
FIG. 6 is a front view illustrating a state of measuring pull strength variation.
Figure 7:
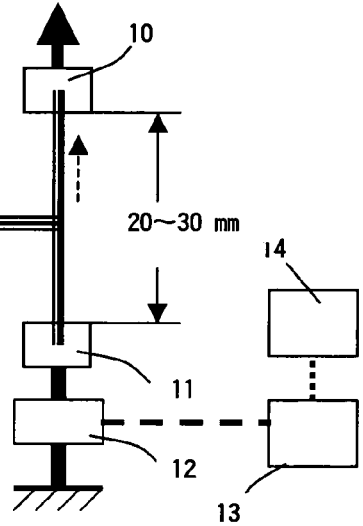
FIG. 7 is a side view illustrating the state of measuring pull strength variation.

Each test piece thus prepared was fixed by jaws 10, 11 of a tensile tester to grasp both free ends, as shown in FIGS. 6 and 7. The tensile tester had a moving jaw 10 and a fixed jaw 11 provided with a force gauge 12. The force gauge 12 was connected to a digital recorder 13 having a personal computer 14. The distance between the jaws 10, 11 was 20–30 mm. Then, the moving jaw 10 was worked to pull the upper free end of the test piece 5 just upward at a constant speed in accordance with JIS Z 0238, and a maximum value of pull strength was recorded.

The maximum pull strength at each temperature was plotted to form a graph shown in FIG. 11 by a full line. The boundary between a peel seal and a rupture seal was at the pull strength lower than the peak by 20% located on the side of a welding surface temperature higher than the peak, i.e.

at 157° C. That is, the peel seal region was lower than 157° C. and the rupture seal region was higher than 157° C.

Figure 8:
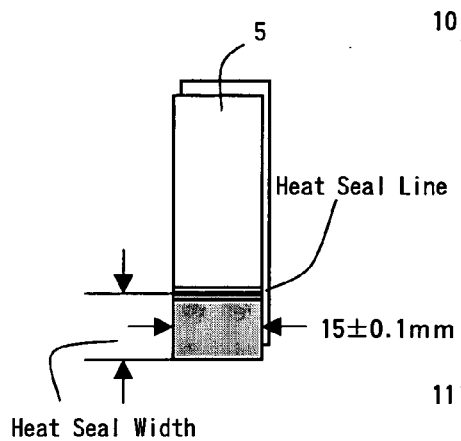
FIG. 8 is a plan view of a test piece for the JIS method used in Example 1.
Figure 9:
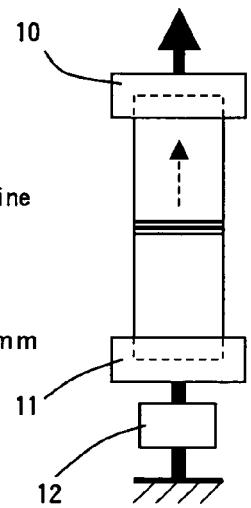
FIG. 9 is a front view illustrating a state of measuring heat-sealing strength variation according to the JIS method.
Figure 10:
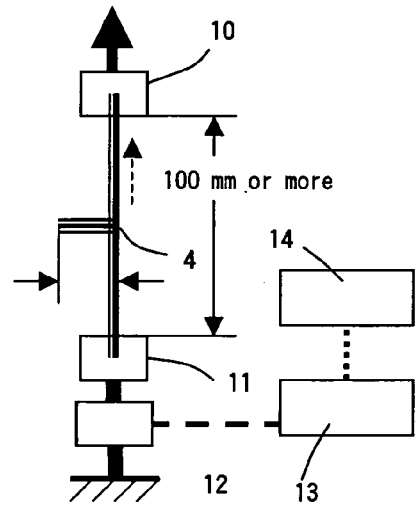
FIG. 10 is a side view illustrating a state of measuring heat-sealing strength variation according to the JIS method.

In comparision, heat-sealing test of the same test piece was conducted according to JIS Z 0238 wherein the heat-sealed test piece is shown in FIG. 8, and pulling conditions are shown in FIGS. 9 and 10. The results are shown in FIG. 11 by a broken line.

It can be seen from the curves in FIG. 11 that the fusion of the heat seal layer began at about 140° C. and was completed at about 153° C.

The data obtained by the JIS method indicates a high heat-sealing strength up to about 175° C., although slightly lowered. On the other hand, according to the method of the invention, the pull strength was sharply decreased from the peak of 153° C., especially around 157° C. Rupture was clearly found around 157° C. by visual observation, and it was confirmed that the discrimination of a peel seal from a rupture seal can be ensured by the method of the invention.

The Food Sanitation Law in Japan requires a heat-sealing strength of 25 N/15 mm or more for retort packaging. From the results of FIG. 8, it can be seen that this requirement can be achieved by a heat-sealing temperature (welding face) in a range from 149° C. to 158° C. In order to resist great impact stress, it is preferable to choose a peel seal region from 149° C. to 155° C.

Heretofore, fundamental packaging functions could not be satisfied entirely by the control of heat-sealing conditions based on the JIS method, and bag rupture or pinhole problems occurred occasionally. By using the method of the invention, discrimination of a peel seal from a rupture seal can be ensured, and bag rupture and pinhole troubles caused by overheating can be removed.

Example 2

Designing of a Heat Seal Width

A commercial sheet for a pouch was subjected to testing which had a layer construction of 12 µm polyethylene terephthalate/15 µm polyethylene/7 µm aluminum/50 µm polyethylene. The polyethylene layer 50 µm in thickness was the heat seal layer having a fusion temperature of about 125° C.

This sheet was cut into strips similar to Example 1 to prepare test pieces.

The heat-sealing tester employed was the same as employed in Example 1.

A suitable heating time was previously measured similar to Example 1, and set for 8 seconds.

Heat-sealing was carried out similar to Example 1, except that the heat-sealing was conducted in the cross direction as shown in FIG. 8.

After heat-sealing, each test piece was cooled similar to Example 1.

Then, both side portions of the cooled test piece were slit leaving a central portion 15 mm in width with an accuracy of ±0.1 mm, and the heat-seal portion was cut so that the heat seal width became 15–20 mm.

The variation of pull strength with peel length of each test piece thus prepared was measured similar to Example 1, except that the distance between the jaws 10, 11 was 20–30 mm. The pulling speed was 100 mm/min.

Figure 12:
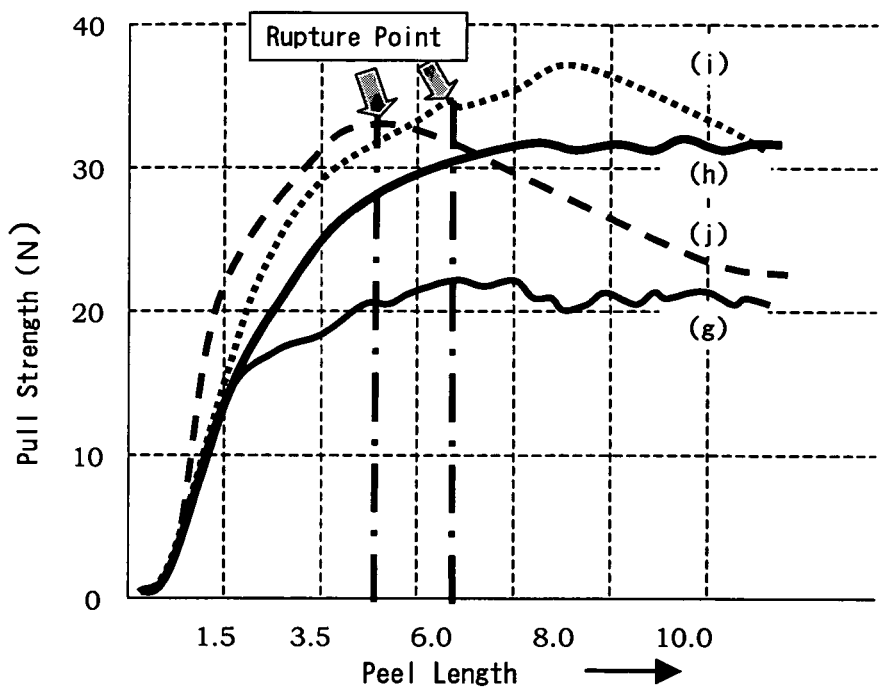
FIG. 12 is a graph showing pull strength variation with peel length obtained in Example 2.

Representative variation patterns of pull strength with peel length at various welding face temperature are shown in FIG. 12. In the figure, g is the case of welding face temperature of 103° C., h is that of 120° C., i is that of 125° C. and j is that of 130° C.

The heat-sealing temperature (welding face temperature) was varied along 11 points from 100° C. to 136° C., and using the personal computer 14, the peel energies of all the temperatures were calculated as to peel lengths of 5 mm, 7.5 mm and 10 mm. In the cases of rupturing or delamination, the peel energy was calculated up to rupturing or delamination.

Figure 13:
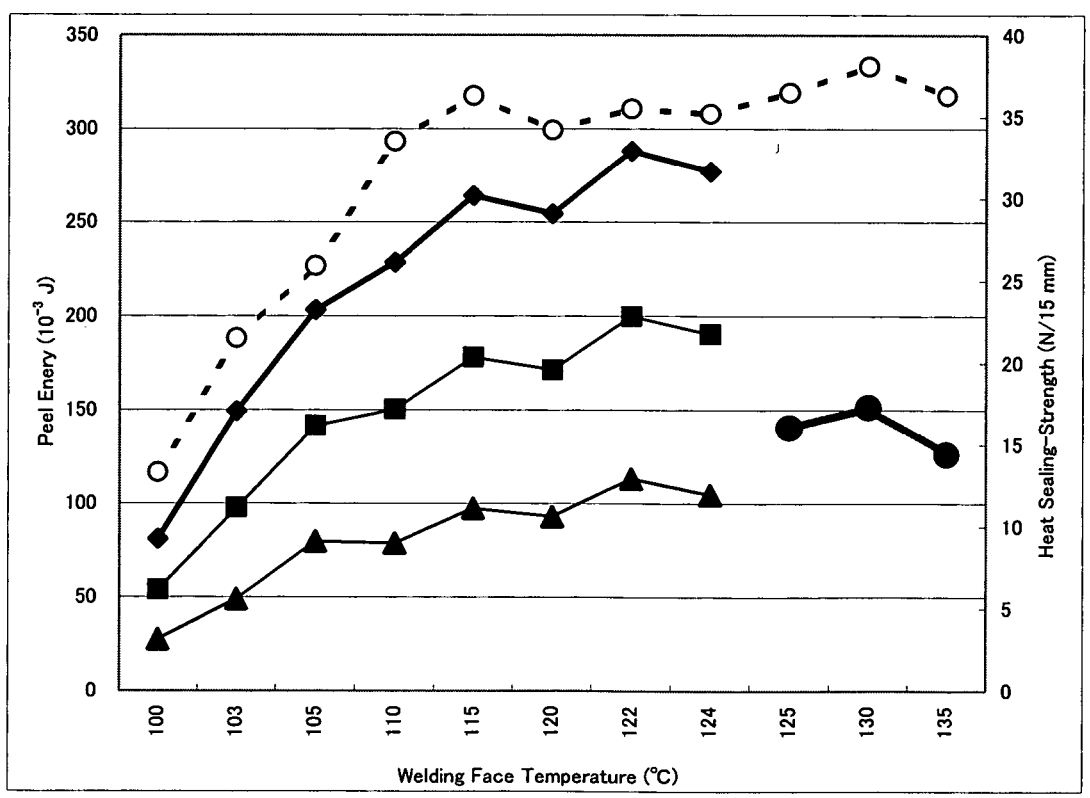
FIG. 13 is a graph showing a relationship between peel energy and heat-sealing temperature as a material for designing heat seal width.

The results are shown in FIG. 13. In the figure, the closed rhombs indicate the case of a peel length of 10 mm, closed squares indicate that of 7.5 mm, closed triangles indicate that of 5 mm, and closed circle indicate the case of a rupture peel.

In comparison, the heat-sealing strength measured by the JIS method is shown in FIG. 13 by the open circles.

As can be seen from FIG. 13, the peel energy in both of a peel length of 7.5 mm and 10 mm exceeds the greatest peel energy of a rupture seal, i.e. $150 \times 10^{-3}$ J. That is, in the case of the heat seal width of 7.5 mm, when the welding face temperature is made in the range from 110° C. to 124° C., the heat sealed portion becomes more resistant to unsealing than a conventional rupture seal. In the case of the heat seal width of 10 mm, when the welding face temperature is in the range from 103° C. to 124° C., the heat sealed portion becomes more resistant to unsealing than a conventional rupture seal. By interpolating the data, it can be seen that a heat seal width of 6 mm heat-sealed at a welding face temperature of 122° C. is equivalent to a conventional rupture seal, as to resistance to unsealing. By employing the heat seal width of 10 mm at a welding face temperature of 122° C., resistance to unsealing can be made nearly twice that of a conventional rupture seal.

Heretofore, fundamental packaging functions could not be satisfied entirely by the control of heat-sealing conditions based on the JIS method, and bag rupture or pinhole problems occurred occasionally. By using the method of the invention, discrimination of a peel seal from a rupture seal can be ensured, and bag rupture and pinhole troubles caused by overheating can be removed.

By employing the invention, generation of bag rupture and pinholes can be prevented by utilizing the load absorbing ability by the peel energy of a peel seal.

What is claimed is:

1. A method of designing a heat seal width which comprises;
   (1) heat-sealing a test piece of a sheet to be heat-sealed at a temperature lower than the fusion temperature of a heat seal portion of the sheet,
   (2) heat-sealing another test piece of the sheet at a temperature at or higher than the fusion temperature,
   (3) pulling to peel a heat-sealed portion of each test piece, and measuring the pull strength variation with peel length,
   (4) calculating the peel energy in various peel lengths of the test piece heat-sealed at a temperature lower than the fusion temperature of the heat seal portion of the sheet by integrating the pull strength variation,
   (5) calculating the peel energy of the test piece heat-sealed at the temperature at or higher than the fusion temperature by integrating the pull strength variation up to rupture at the heat-sealed portion, and
   (6) setting the heat seal width at a peel length having a peel energy higher than the peel energy of the test piece heat-sealed at a temperature at or higher than the fusion temperature.

2. The method of claim 1 wherein the temperature lower than fusion temperature is lower than the fusion temperature by 1 to 20° C.

3. The method of claim 1 wherein the temperature at or higher than the fusion temperature is at or higher than the fusion temperature by 10° C.

4. The method of claim 1 wherein the temperature lower than fusion temperature and the temperature at or higher than the fusion temperature is measured at a welding face to be bonded by heat-sealing.

5. A method of designing a heat seal width which comprises;
   (1) repeating heat-sealing of test pieces of a sheet to be heat-sealed at varying heat-sealing temperatures around the fusion temperature of a heat seal portion of the sheet,
   (2) pulling to peel a heat-sealed portion of each test piece, and measuring the pull strength variation with peel length,
   (3) calculating the peel energy in various peel lengths of each test piece at each heat-sealing temperature lower that the fusion temperature by integrating the pull strength variation to determine a variation of the peel energy with the heat-sealing temperature at various peel lengths,
   (4) calculating the peel energy of at least one test piece heat-sealed at a temperature at or higher than the fusion temperature by integrating the pull strength variation up to rupture at a heat-sealed portion, and
   (5) setting the heat seal width at a peel length having a peel energy higher than the peel energy of the test piece heat-sealed at a temperature at or higher than the fusion temperature.

6. The method of claim 5 wherein the peel energy of the test piece heat-sealed at a temperature at or higher than the fusion temperature is a maximum peel energy thereof.

7. A method of distinguishing peel seals with a rupture seal which comprises;
   (1) repeating heat-sealing of test pieces of a sheet to be heat-sealed obliquely with varying heat-sealing temperatures around the fusion temperature of heat seal portion of the sheet,
   (2) pulling to peel a heat-sealed portion of each test piece, and measuring the pull strength variation with peel length to determine a maximum pull strength,
   (3) plotting the maximum pull strength against heat-sealing temperature, and
   (4) determining the position of a pull strength lower than the peak of the maximum pull strength by 20%, which is set from experimental results, by considering experimental error on the side of a higher heat-sealing temperature than the peak.

8. The method of claim 7 wherein the angle of the heat-sealed portion is 10 to 70 degrees against the cross direction of the test piece.

9. A method of designing a heat seal width which comprises;
   (1) repeating heat-sealing of test pieces of a sheet to be heat-sealed obliquely with varying heat-sealing temperatures around the fusion temperatures of a heat seal portion of the sheet,
   (2) pulling to peel a heat-sealed portion of each test piece, and measuring the pull strength variation with peel length to determine a maximum pull strength,
   (3) plotting the maximum pull strength against heat-sealing temperature, and
   (4) determining the position of a pull strength lower than the peak of the maximum pull strength by 20% which is set from experimental results by considering experimental error on the side of a higher heat-sealing temperature than the peak,
   (5) calculating the peel energy in various peel lengths of the test piece at a temperature lower than the position by integrating the pull strength variation,
   (6) calculating the peel energy of the test piece at a temperature at the position or higher than that by integrating the pull strength variation up to rupture at heat-sealed portion, and
   (7) setting the heat seal width at a peel length having a peel energy higher than the peel energy obtained in (6).

* * * * *